US010265481B2

United States Patent
Islam

(10) Patent No.: US 10,265,481 B2
(45) Date of Patent: Apr. 23, 2019

(54) INTRAMARROW INJECTION/INFUSION AND ASPIRATION NEEDLE AND METHOD

(71) Applicant: Abul Bashar Mohammad Anwarul Islam, Amherst, NY (US)

(72) Inventor: Abul Bashar Mohammad Anwarul Islam, Amherst, NY (US)

(\*) Notice: Subject to any disclaimer, the term of this patent is extended or adjusted under 35 U.S.C. 154(b) by 240 days.

(21) Appl. No.: 15/341,540

(22) Filed: Nov. 2, 2016

(65) Prior Publication Data
US 2018/0117262 A1    May 3, 2018

(51) Int. Cl.
*A61M 5/32*    (2006.01)
*A61B 10/02*   (2006.01)
(Continued)

(52) U.S. Cl.
CPC ......... *A61M 5/3286* (2013.01); *A61B 10/025* (2013.01); *A61B 10/0283* (2013.01); *A61M 5/31* (2013.01); *A61M 5/329* (2013.01); *A61B 17/3472* (2013.01); *A61B 2010/0258* (2013.01); *A61M 5/158* (2013.01); *A61M 5/1582* (2013.01);
(Continued)

(58) Field of Classification Search
CPC .............. A61M 5/3286; A61M 5/3295; A61M 5/3293; A61M 5/329; A61M 5/3291; A61M 5/158; A61M 5/1582; A61M 2005/1581; A61M 2005/1586; A61M 2202/10;
(Continued)

(56) References Cited

U.S. PATENT DOCUMENTS

| 5,176,643 A * | 1/1993 | Kramer ............... A61M 5/2033 604/135 |
| 6,849,051 B2 * | 2/2005 | Sramek ............... A61B 10/025 600/565 |

(Continued)

OTHER PUBLICATIONS

Islam A. (1982). Bone marrow structure in human leukaemias: A histological study by plastic embedding techniques. Ph.D. Thesis. University of London.
(Continued)

*Primary Examiner* — Devin B Henson
(74) *Attorney, Agent, or Firm* — Vincent G. LoTempio; Kloss, Stenger & LoTempio; David T. Stephenson

(57) ABSTRACT

A method and apparatus for injecting supportive and therapeutic agents into bone marrow. During conventional chemotherapy for leukemia, lymphoma, multiple myeloma and other bone related diseases, chemotherapeutic agents are typically injected intravenously. Intravenous injection, however, as a method of chemotherapy, has a number of potential disadvantages. By injecting therapeutic agents directly into the bone marrow using the present method and apparatus, these disadvantages can be avoided. A stronger needle with a shorter and sharper tip, when compared to a conventional intravenous or sternal puncture needle, designed to optimally administer therapeutic agents into bone marrow without causing injury is disclosed. The method includes injecting therapeutic agents into large reservoirs of bone marrow in accessible areas such as ilium and sternum is most likely to have a significant effect in treating bone marrow diseases. The needle may have side holes for wider and more even distribution of therapeutic agents throughout the marrow.

14 Claims, 11 Drawing Sheets

(51) Int. Cl.
*A61B 17/34* (2006.01)
*A61M 5/158* (2006.01)
*A61M 5/31* (2006.01)

(52) U.S. Cl.
CPC ......... *A61M 5/3293* (2013.01); *A61M 5/3295* (2013.01); *A61M 2005/1581* (2013.01); *A61M 2005/1586* (2013.01); *A61M 2202/10* (2013.01); *A61M 2210/02* (2013.01)

(58) Field of Classification Search
CPC .............. A61B 10/025; A61B 10/0283; A61B 2010/0258; A61B 17/3472
See application file for complete search history.

(56) References Cited

U.S. PATENT DOCUMENTS

| | | | | |
|---|---|---|---|---|
| 8,668,698 | B2* | 3/2014 | Miller | A61B 10/025 408/238 |
| 9,949,777 | B2* | 4/2018 | Sweeney | A61B 17/7061 |
| 2004/0220497 | A1* | 11/2004 | Findlay | A61B 10/025 600/562 |
| 2004/0260250 | A1* | 12/2004 | Harris | A61M 5/158 604/263 |
| 2010/0030105 | A1* | 2/2010 | Noishiki | A61B 10/025 600/567 |
| 2017/0311981 | A1* | 11/2017 | Real | A61B 17/164 |

OTHER PUBLICATIONS

Islam A (1992). The Origin and Spread of Human Leukemia. Medical Hypothesis 39: 110-118.
Islam A (1985). Haemopoietic Stem Cell: A New Concept. Leukemia Research 9:(11) 1415-1432.
Islam A, Takita H (2012). Malignant Pleural Effusion and Advanced Stage Low-Grade Non-Hodgkin's Lymphoma Successfully Treated with Intrapleural Instillation of Rituximab. Blood 120:4891.
Hughes RG, Islam A, Lewis SM, Catovski D (1981) Spontaneous remission following bone marrow necrosis in chronic lymphocytic leukemia. Clin Lab Hematol 3:174-184.
Islam A. (2015). Induction treatment of acute myeloid leukemia in an elderly patient with intramarrow injection/administration of cytarabine: first report of a case. Clinical Case Reports 3(12): 1026-1029.
Stone RM. (2002). The Difficult Problem of Acute Myeloid Leukemia in the Older Adult. CA Cancer J Clin. 52:363-371.
Islam A. (2016). A New Posterior Iliac Intramarrow Injection/Aspiration Needle. Islam A. J Clin Pathol 0:1-3. doi:10.1136/jclinpath-.
Fenaux P, Mufti GJ, Lindberg EH, Santini V, Gattermann N, Germing U, Sanz G, List AF, Gore S, Seymour JF, Dombret H, Baxkstrom J, Zimmerman L, Mckenzie D, Beach CL, and Silverman LR. (2010). Azacitidine Prolongs Overall Survival Compared With Conventional Care Regimens in Elderly Patients With Low Bone Marrow Blast Count Acute Myeloid Leukemia. J Clin Oncol. 28:562-569.
Zhang WG, Wang FX, Chen YX, Cao XM, He AL, Liu J, Ma XR, Zhao WH, Liu AH, and Wang JL. (2007). Combination chemotherapy with low-dose cytarabine, homoharringtonine, and granulocyte colony-stimulating factor priming in patients with relapsed or refractory acute myeloid leukemia. Am J Hematol. 83:185-188.

* cited by examiner

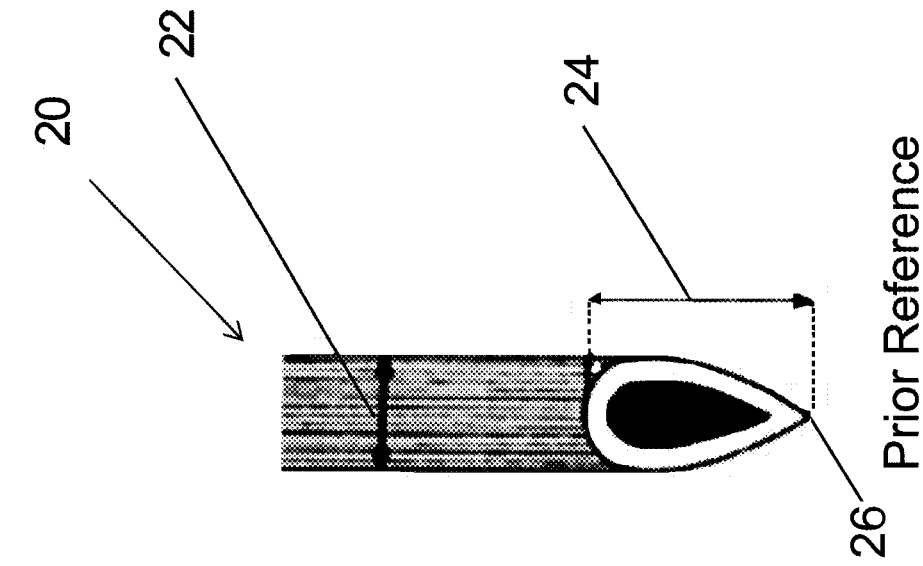
FIG.1B Prior Reference
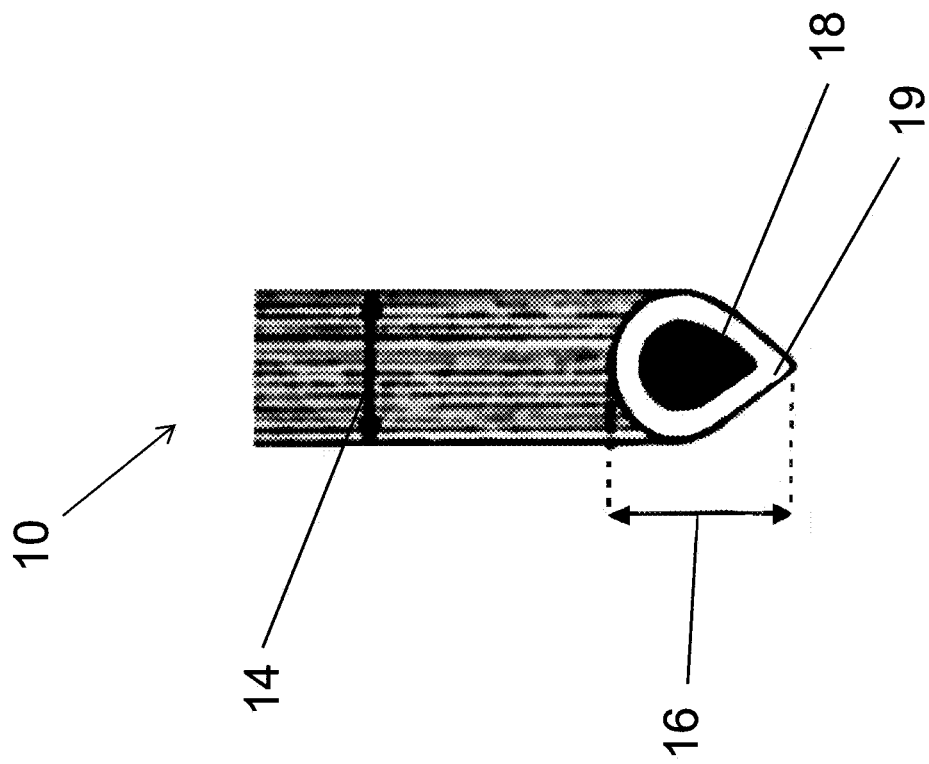
FIG.1A

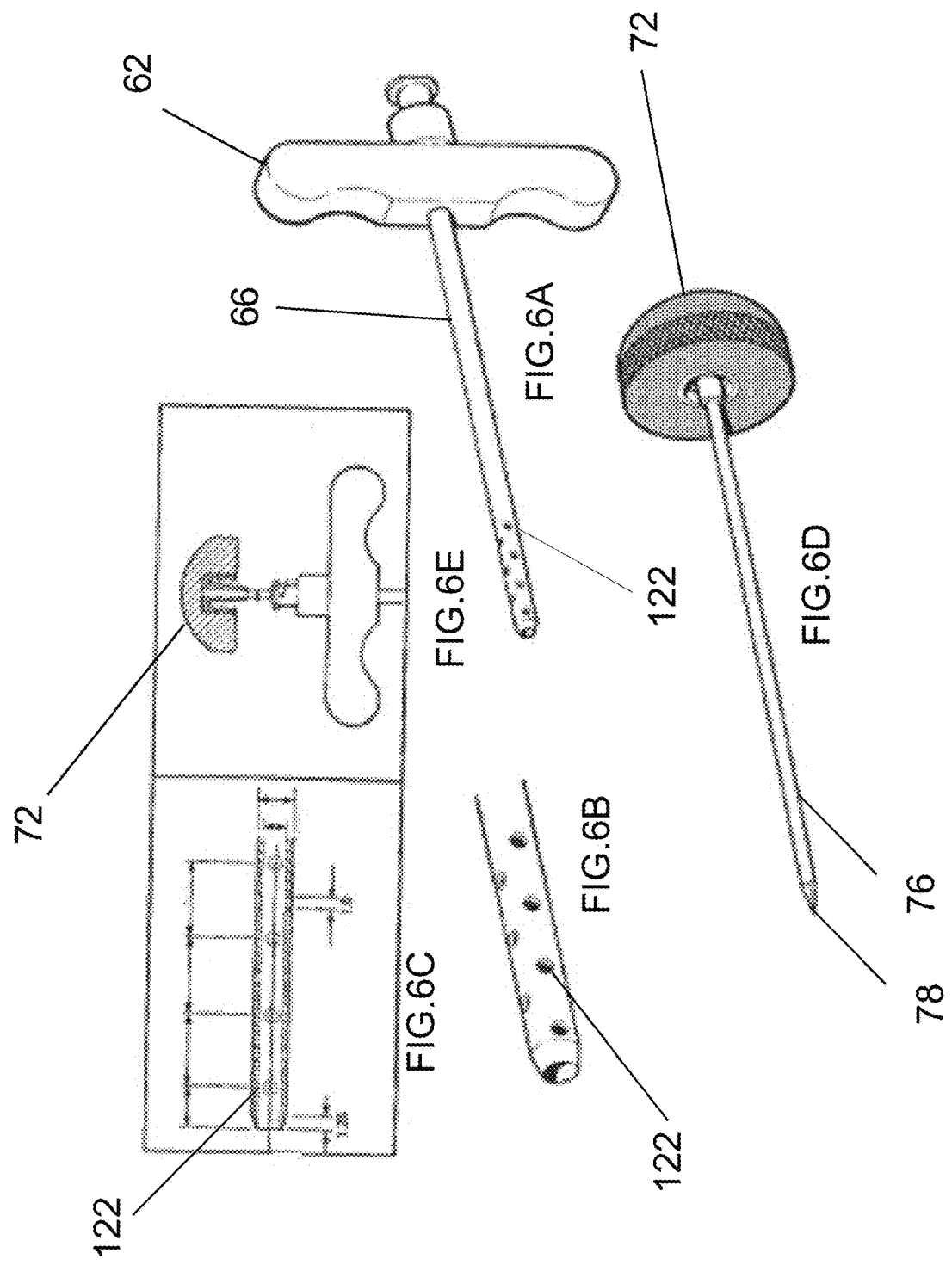

INTRAMARROW INJECTION/INFUSION AND ASPIRATION NEEDLE AND METHOD

FIELD

The present disclosure relates to a method and apparatus for injecting supportive and therapeutic agents into bone marrow, while also aspirating bone marrow for diagnostic, research and investigative purposes. In particular, the present disclosure relates to methods and apparatuses for introducing supportive and chemotherapeutic agents into bone marrow.

BACKGROUND

The statements in this section merely provide background information related to the present disclosure and may not constitute prior art.

During chemotherapy, chemotherapeutic agents are typically injected intravenously. Intravenous injection, however, as a method of chemotherapy, has a number of potential disadvantages. These include delivery of potentially toxic chemotherapeutic agents to non-target regions of the body and a requirement for high doses of chemotherapeutic agents due to dilution, metabolism, and degradation of the drug throughout the body. Therefore, the injection of a drug directly into a target region affected by disease is desirable.

A number of diseases afflict the bone marrow specifically. These include leukemia, lymphoma and multiple myeloma, among others. These cancers are typically treated by intravenous chemotherapy. The intravenous method of delivery suffers from the limitations of intravenous therapy discussed above. Vascular injection results in only a small percentage of the agent reaching the target organ, or in this case, the marrow. This can lead to detrimental side effects due to the amount of agent necessary to inject into a vascular environment in order for an effective amount to reach the marrow. Thus, there is a need for improved devices and methods for effectively injecting therapeutic agents directly into the marrow.

Direct injection of chemotherapeutic agents into the bone marrow is not a method that has been established in the art. The use of needles to penetrate the bone to aspirate bone marrow is well-known in the art. Bone marrow aspiration is a procedure used to obtain the blood-forming portion (marrow) of the inner core of bone for examination in a laboratory or for transplantation. The procedure often includes inserting a needle into a bone that contains marrow and withdrawing the marrow.

The needles available for aspiration of bone marrow are not sufficient for the injection of therapeutic agents into the sternal bone marrow. Therefore, there is a need for a needle designed specifically for intramarrow injection/infusion that can also remain in the marrow for an extended period of time, such as a week or longer.

In order to determine whether intramarrow injection could be an effective method of treating bone marrow disease, initial studies in understanding bone marrow pathology in normal and diseased condition were conducted. (Islam A. 1982. Ph.D. Thesis. University of London.) These early studies resulted in a new method of fixing bone and bone marrow biopsies in a special fixative. Specimens fixed in Schaeffer's solution provides better cytomorphological details and specimens fixed in Bouin's solution are optimal for cytochemical and immunological studies, when compared to conventional 10% formalin.

Following fixation the bone and bone marrow biopsies were processed in plastic (methyl and glycol methacrylate) and semi-thin sections (1-2 micron thick) were obtained from these plastic embedded bone and bone marrow biopsies (BMB) using a special microtome. Unlike the conventional paraffin embedded biopsy sections which are thick (5-10 micron), these semi-thin sections of plastic embedded bone and bone marrow biopsies, when stained with Romanowsky stain, provide cellular morphology and structural details of the marrow in much greater detail than hitherto possible.

Research conducted by Islam using the plastic embedding method, resulted in the observation that the interface between the bone and marrow is not dissociated/separated but remains intact and the endosteal cells which line the bony trabeculae were clearer and did not become deformed or displaced like the cells would using the existing and conventional formalin fixed paraffin embedding method. The clear picture, close to what is observed in situ, of cell biology in the bone marrow produced by these studies showed for the first time the significance of the endosteal region in the origin and the spread of leukemia (Medical Hypothesis 39: 110-118 (1992), Leukemia Research 9:(11) 1415-1432 (1985)).

Based in part on observations of the endosteal cells in plastic embedded BMB sections from normal adults as well as from patients with various hematological disorders such as leukemia, lymphoma, multiple myeloma, aplastic anemia, and myelodysplastic syndrome, Islam postulated that the endosteal cells are reminiscent of embryonal stage mesenchymal cells and, depending on the needs of the body, may differentiate into either myeloid, lymphoid, stromal or fat cells. Further, the endosteal cells may become osteoclasts and osteoblasts (bone forming cells). In leukemias, particularly in acute myeloid leukemia (AML), Islam observed that the leukemic blast cells in AML were originating from the endosteal region. In some instances the endosteal cells appeared to be giving rise to the leukemic blast cell population (Medical Hypothesis 39: 110-118 (1992), Leukemia Research 9:(11) 1415-1432 (1985)).

These observations prompted investigation into a potential treatment of leukemia through injection of chemotherapeutic agents directly into the marrow cavity, where leukemia originates, rather than the conventional intravenous method of delivery. Intramarrow injection of drugs could potentially improve delivery of the drugs to the necessary cells, thereby improving the outcome and response to therapy for such patients.

SUMMARY

The present disclosure teaches a method and apparatus for effectively introducing therapeutic agents into bone marrow using novel needle design in conjunction with a novel method of injection. The needles used in the method and apparatus of the present disclosure are comprised of a specially designed material, and sternal needle of the present disclosure has a tip and handle designed for the method herein disclosed. The handle of the needle apparatus has a foldable, winged design. The needle is mounted to the handle in a manner that allows convenient manipulation of the needle for penetration of the bone. The needle has a tip at a first end and a portion proximate to a second end. The tip of the bone marrow treatment needle is of shorter length than a typical vascular/sternal needle, and has sharpness necessary for penetrating a sternal bone. The method of preparing the patient and rotating the bone marrow treatment needle during its introduction and injection provides efficient, pain free, safe and effective method of treatment.

The advantages of intramarrow injection/infusion needle are numerous. Direct injection into the bone marrow allows for treatment when veins are collapsing. Direct injection into the marrow delivers more active agent to the treatment location without dilution or degradation that can be caused by intravenous injection. Further, direct injection into the marrow potentially allows for vascular transport of a drug to regions of the bone marrow away from the target site due to the highly vascularized nature of the bone marrow region, without causing a high degree of systemic distribution of the drug to non-target regions.

Support for the premise that direct injection of a drug into a target disease region can lead to transport and wider distribution of the drug throughout the target organ is found in a study conducted by Islam and Takita (Blood 120:4891 (2012)). Here, a chemotherapeutic agent was introduced directly into the intrapleural region surrounding the lung, rather than intravenously, to treat a patient with Non-Hodgkins Lymphoma. In this study 100 mg of rituxan was injected into the intrapleural region for treatment, rather than the 500 mg of rituxin typically administered intravenously for chemotherapeutic treatment. The results of the study indicated that the chemotherapeutic agent was successfully delivered to the intrapleural region, and was distributed systemically to a degree that treatment of diseased cells away from the direct injection site was occurring successfully. The success achieved in the study in both method and outcome suggests that direct injection to a target site can be an effective method of chemotherapy.

In the present disclosure, intramarrow injection is shown to be an effective method of treating bone marrow disease. The method of the present disclosure includes intramarrow injection into the sternum and the pelvic bone. The sternum and pelvic region are largest readily accessible reservoirs of bone marrow superficial to the body. Injection into these areas allows the drug to treat these primary regions directly, in addition to treating other affected regions of bone marrow because a portion of the injected agent will be absorbed through the rich venous sinusoids of the marrow cavity and will travel to other distant marrow regions almost as effectively as when given by an intravenous route. This method results in reduced toxicity for already compromised patients who may not be able to tolerate standard dosages of chemotherapy drugs injected intravenously. The benefit of reduced toxicity is due to the lower dose of drug required as well as the lack of dispersion of drugs at high concentration to non-target areas.

An additional therapeutic benefit of intramarrow injection results from the induction of necrosis within the marrow caused by the relatively large dose and high concentration of chemotherapeutic agent present in the marrow after injection. The large dose of agent at the target site will result in necrosis, which can assist in destruction of, and reduction of, malignant cells and summon macrophages to further destruction of target cells. The destruction of malignant cells (necrosis) may summon macrophages and may foster further destruction of target cells. The localized process may also affect the micro-environmental cells that control hematopoiesis and immune-regulatory cells that control the immune functions. The overall combined effects may initiate beneficial outcome not available through conventional modes of treatment.

The theory that necrosis could have a therapeutic effect on cancerous bone marrow is supported by a study performed by Hughes et al. (Clin Lab Hematol 3:174-184(1981)). In this study, the authors noted that bone marrow necrosis was evident in a 58 year old patient diagnosed with chronic lymphocytic leukemia (CLL). Bone marrow necrosis is rarely observed in living patients, regardless of disease state. The patient was not given chemotherapy and was placed under observation.

Within months, the CLL patient with necrosis showed an unexpected recovery both clinically and hematologically. Diseased regions of bone marrow spontaneously resolved to normal and the patient's lifespan was unexpectedly prolonged. From this observation, Islam postulated that necrosis could result in an enhanced recovery due to extensive cell death among diseased cells and an immune response to the region.

This result, combined with the study showing distribution of drug from the injection site in the intrapleural region suggests the potential for a synergistic effect for intramarrow injection of therapeutic agents for bone marrow disease. The combined effect of direct exposure to high doses of chemotherapeutic agent at the target site, vascular transport of the drug from the target injection site to other affected areas, and the necrosis induced at the target site indicates in a synergistic effect in reduction of diseased cells. While chemotherapeutic agents are likely the primary cause of necrosis in the marrow after injection, mechanical disruption of the cells caused by injection of the needle may also be a contributing factor.

As described in Example 1, Islam tested the method of the present disclosure in a clinical setting (Clinical Case Reports 3(12): 1026-1029 (2015)). In this study, specially designed needles and needle assemblies were used to inject a chemotherapeutic agent into the bone marrow of the sternum and the posterior ilium. The needles used in the sternum and ilium of the patient were designed to penetrate the bone through manual manipulation of the needle assembly. The structure and material comprising the needle are uniquely designed for the present disclosure. The needles are comprised of a material designed to maintain a required sharpness during penetration of the bone. The needles tips have a shorter length than a typical vascular injection needle. Further, in one embodiment, the iliac needle is fluted to allow for penetration of a thicker and harder bone than the sternum. The tip of the needle of the present disclosure is designed to minimize the need for force while also creating an efficient means of injection without undue effort by the medical practitioner.

For the present disclosure, different needles are designed for effective penetration of both the sternum and the posterior iliac bones. As described in Example 1, introduction of chemotherapeutic agents at both of these locations was demonstrated to successfully treat and cause reduction of cancer cells throughout the bone marrow, even at regions distal to the injection site.

The assembly of the sternal intramarrow injection/infusion needle (IMIN) includes a butterfly handle that allows for a tight grip by a user. The rotational motion applied to the needle as described in the present disclosure is aided by the design of the handle and the specifications and material of the needle, which combine to form the needle assembly.

In general terms, the method of the present disclosure includes the following: preparing and anesthetizing the region around the injection site; placing the needle at the appropriate site on the bone; applying pressure to the needle; and alternately rotating the assembly in a first and second direction. With regard to the sternum needle, pressure is applied with the needle to the bone until a 'sudden give' sensation is felt by the physician. The depth of the needle is dictated by the skill of the physician and the size of the needle; however, in some embodiments markers or barriers may be used to assist the physician in achieving a proper depth of injection.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

FIG. 1A shows a side view of a sternal intramarrow injection/infusion needle according to the present disclosure;

FIG. 1B shows a side view of a conventional prior reference sternal puncture needle;

FIG. 6A shows a side perspective view of the posterior iliac intramarrow injection/infusion needle with a T-bar handle;

FIG. 6B shows a magnified side perspective view of the posterior iliac intramarrow injection/infusion needle and multiple apertures near the distal end of the needle;

FIG. 6C shows a cross sectional side view of the posterior iliac intramarrow injection/infusion needle and multiple apertures near the distal end of the needle;

FIG. 6D shows a side perspective view of the posterior iliac intramarrow injection/infusion needle stilette;

FIG. 6E shows a cross sectional view of the T-bar and dome handle of the posterior iliac intramarrow injection/infusion needle assembly;

DETAILED DESCRIPTION

Figure 2:
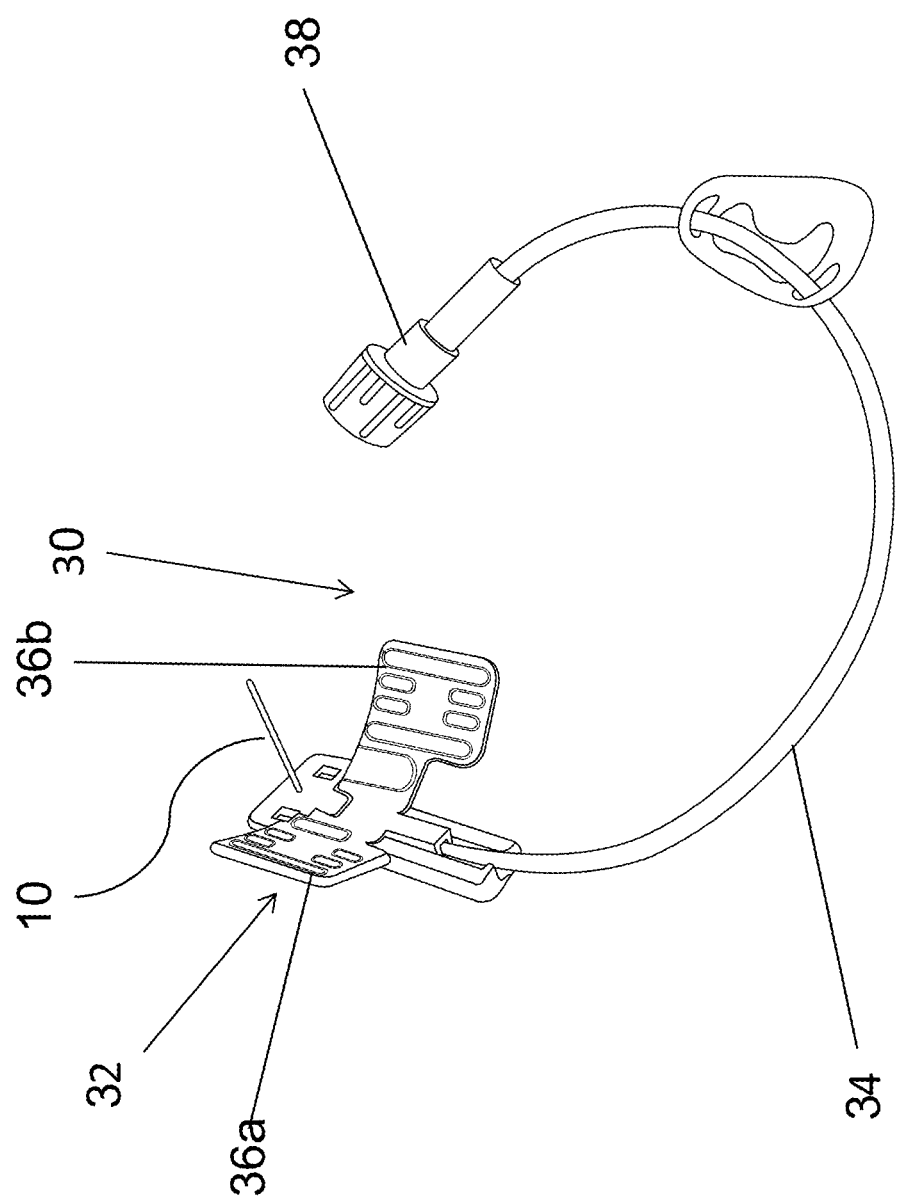
FIG. 2 shows a perspective view of a sternal intramarrow injection/infusion needle assembly.

An intramarrow injection/infusion apparatus and method described below is able to introduce therapeutic agents into bone marrow to treat a wide variety of marrow related disease. The apparatus may be utilized to treat diseases including, but not limited to, acute and chronic leukemia's, Myelodysplastic Syndromes (MDS), Hodgkin's disease (HD) and Non-Hodgkin's Lymphoma (NHL), Multiple Myeloma, and metastatic tumors of the bone.

In one embodiment of the present disclosure, intramarrow injections occur at multiple locations, although the method is not limited to multiple injection locations. In a preferred embodiment the intramarrow injections occur at the sternum and the posterior ilium. This approach involves puncturing the sternum and the posterior ilium with specially designed needles. For injection into the posterior ilium, the needle and assembly differ from the needle and assembly used for sternal injection. Embodiments of the intramarrow injection apparatus are shown in the views of FIGS. 1-11.

The sternal intramarrow injection/infusion needle (IMIN) is shown in FIG. 1A. In a preferred embodiment, sternal intramarrow injection/infusion needle 10 will have a bore 18 of 18 G, although in various embodiments the bore 18 may vary from 27 G to 13 G. The preferred length of the sternal intramarrow injection/infusion needle 10 will be 2.5 inches, although in other embodiments the length sternal intramarrow injection/infusion needle 10 may vary from ½ inch to 4 inches, and may depend on the size of the patient, due to weight, age or other factors. For a typical adult sternum, 2.5 inches provides the proper proportional needle length. Sternal intramarrow injection/infusion needle 10 has a bone penetrating tip 19 of a shorter tip length 16 than the longer tip length 24 of a conventional tip 26 of a conventional prior reference needle 20, as shown in FIG. 1B. The IMIN width 14 of the sternal intramarrow injection/infusion needle 10 may be the same as the conventional width 22 of a conventional needle 20.

In the preferred embodiment of the present disclosure, sternal intramarrow injection/infusion needle 10 is comprised of stainless steel of implantable grade. In one embodiment of the present disclosure, the sternal intramarrow injection/infusion needle 10 is beveled toward bone penetrating tip 19. The beveled bone penetrating tip 19 of the sternal intramarrow injection/infusion needle 10 allows for easy penetration of the skin, soft tissue and the anterior plate (cortical) of the sternum. The shorter tip length 16, relative to the longer tip length 24 of a conventional needle, lowers risk of through and through penetration of the sternum or accidental passage through the posterior plate of the sternum thus injuring the great blood vessels that lie underneath.

To prevent over penetration of the sternum during sternal puncture, sternal intramarrow injection/infusion needle 10 may have a guard. As a safety precaution a guard, smaller in construction than a typical needle guard, may be attached to the intramarrow injection/infusion needle 10. Alternatively, the sternal intramarrow injection/infusion needle 10 may be marked with circular line every few millimeters or centimeters along the length of the needle. These markings can provide a guideline for how far the sternal intramarrow injection/infusion needle 10 can, or should, be introduced once it makes contact with the cortical bone. The thickness of the anterior plate of the sternum may vary from patient to patient, creating the need for adjustment during puncture based on physician observation. The thickness of the anterior plate of the sternum is usually between five to 10 mm although the safety mechanisms may be customized for thicker or narrower sternum widths.

As shown in FIG. 2, sternal intramarrow injection/infusion needle 10 may preferably be connected with plastic tubing 34, the diameter of which will vary according to the gauge of the sternal intramarrow injection/infusion needle 10. The length of plastic tubing 34 may vary from 2 to 10 inches. The distal end of the plastic tubing 34, away from the intramarrow injection/infusion needle 10, will have an attachment device 38 to accept luer and non-luer lock syringes. Attachment device 38 will have a cap which has to be removed before injection of materials or aspiration of marrow. Alternatively the device of the present disclosure may be covered with a diaphragm which will withstand repeated puncturing by needles. The distal portion of plastic tubing 34 may be V shaped with capped attachments at both ends for dual purposes when one line can be used for aspiration and the other line can be used for injection of materials into the marrow cavity.

Sternal intramarrow injection/infusion needle 10 is connected to handle 32 having winged portions 36a and 36b to form, along with the attached plastic tubing 34, sternal IMIN needle assembly 30. Handle 32 is folded and gripped by winged portions 36a and 36b during use.

Figure 3:
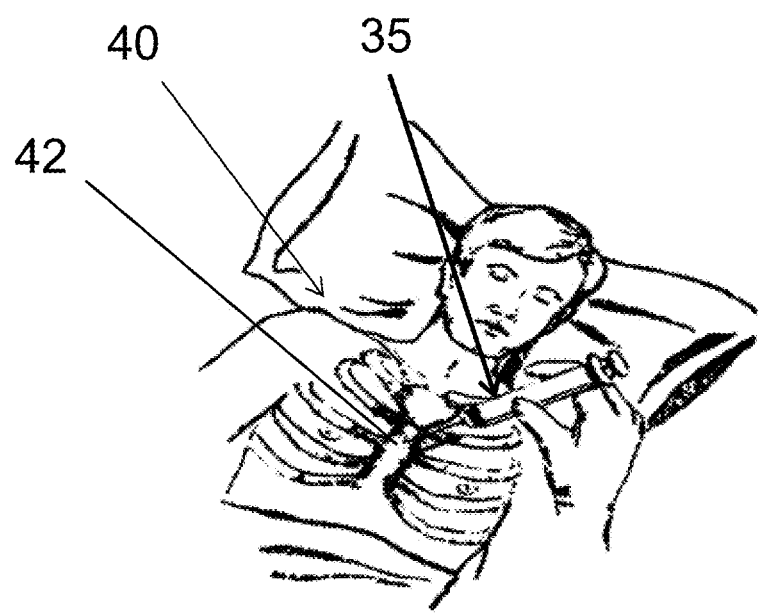
FIG. 3 shows a perspective view of the location of injection of anesthetic into the sternal region.

With regard to FIG. 3, the initial step of anesthetic injection at the site for sternal injection/infusion is illustrated. The patient 40 is first placed on his back with the head and neck comfortably flexed and resting on a soft low-lying pillow. In men, it may be necessary to shave the skin over the sternum prior to the introduction of the needle/procedure. In adults the intramarrow injection/infusion needle 10 should be introduced in the proximal region of the body of the sternum 42, at the level of the second intercostal space, in the mid-sternal line. Prior to injection, it may be useful to probe the injection site with a 21 gauge, one and a half inch needle to feel the depth at which the sternum 42 will be struck (with or without the attached syringe) and to roughly assess the effect of an anesthetic injected by an anesthetic syringe 35, which is applied prior to injection. The probing is typically performed with the same needle used to inject the anesthetic that is attached to anesthetic syringe 35. No skin incision is necessary for this procedure.

Figure 4A:
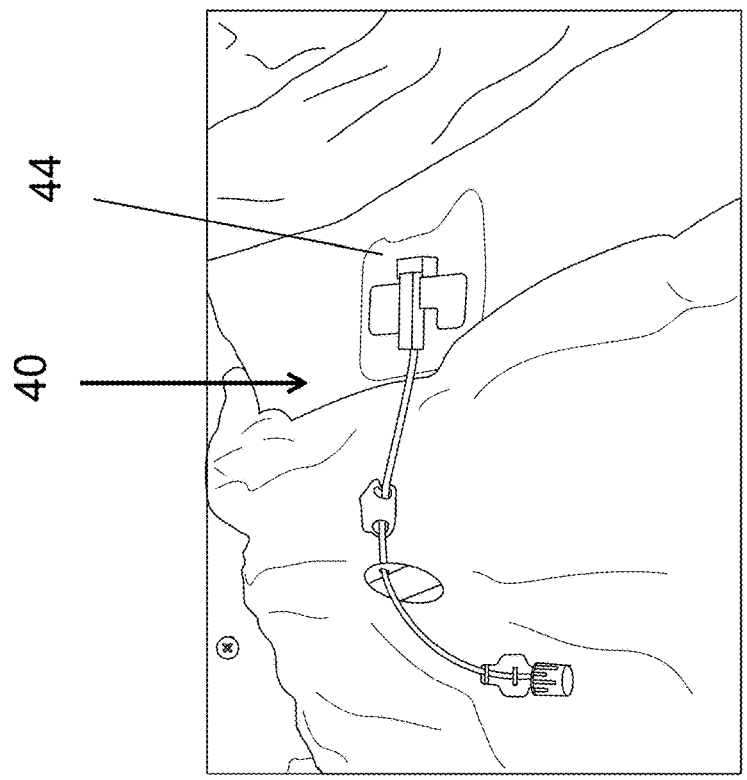
FIG. 4A shows a perspective view of sternal intramarrow injection/infusion needle assembly being placed for sternal puncture.

As shown in FIG. 4A, prior to injection, IMIN needle assembly 30 is held with winged portions 36a and 36b between the thumb and the index finger with sternal intramarrow injection/infusion needle 10 pointing towards the sternum 42. After skin sterilization and local anesthesia of the skin, subcutaneous tissue and periosteum the sternal intramarrow injection/infusion needle 10 is slowly advanced towards the sternum 42 so as to hit the cortical bone 52 (shown in FIG. 5) at a right angle. The method of inserting sternal intramarrow injection/infusion needle 10 into the sternal marrow cavity involves folding and gripping the soft flexible winged portions 36a and 36b of needle assembly by the thumb and index finger and applying forward pressure to the intramarrow injection/infusion needle 10 by hand, while at the same time rotating intramarrow injection/infusion needle 10 in a clockwise and counter-clockwise motion of the hand, wrist and arm. As the intramarrow injection/infusion needle 10 is introduced into the sternum 42 a reciprocal clockwise/counter-clockwise rotation improves penetration of sternal intramarrow injection/infusion needle 10 through the cortical bone and into the marrow cavity as sternal intramarrow injection/infusion needle 10 is advanced. The pressure needed to penetrate the cortical bone will depend on the thickness and hardness of the bone.

When sternum 42 is reached it is then penetrated by gentle rotary (clockwise/counterclockwise) motion of sternal intramarrow injection/infusion needle 10. With regard to the number of rotations, only 2 rotations are typically required for penetration, or potentially 3 to 7 depending on the hardness of the bone and the approximate diameter of the circles made during rotation. With regard to the range of rotation IMIN needle assembly 30, the assembly may rotate from 9 o'clock to 3 o'clock clockwise and 3 o'clock to 9 o'clock anti-clockwise in rotary motions. Feedback may indicate to the physician when to alter or stop the motion during insertion of the needle; for example, if the patient complains of pain, then the area was not properly anesthetized and more anesthetic may be needed.

Upon entry of sternal intramarrow injection/infusion needle 10 into the sternal marrow cavity 54 (shown in FIG. 5) a sudden 'give' is felt by the physician. The "sudden" give of the needle indicates that the cortical bone 52 has been perforated. Once the cortical bone 52 has been penetrated, sternal intramarrow injection/infusion needle 10 is advanced only a few millimeters into the sternal marrow cavity 54 with gentle, reciprocal clockwise/counter-clockwise rotary motion.

Figure 4B:
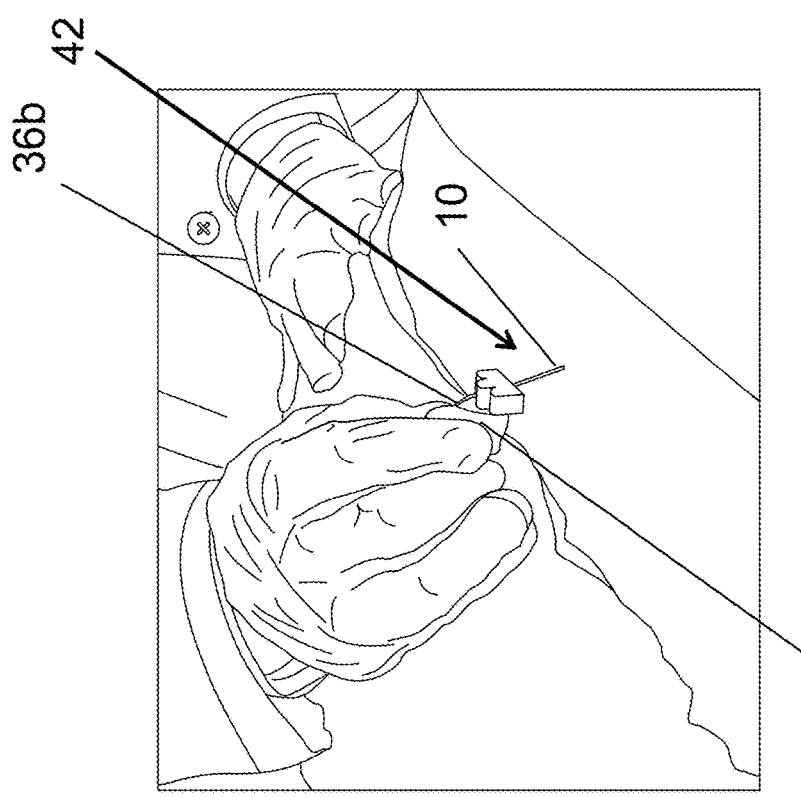
FIG. 4B shows a perspective view of sternal intramarrow injection/infusion needle assembly affixed to a patient with an adhesive tape.

As shown in FIG. 4B, once sternal intramarrow injection/infusion needle 10 is in place, after it has penetrated the cortical bone 52 and entered into the sternal marrow cavity 54, it is held in position with left or right hand. The foldable winged portions 36a and 36b are then unfolded from a vertical wing gripping configuration (winged grip) into a horizontal wing attachment configuration, and sternal IMIN needle assembly 30 is secured to the patient's chest wall 40 with appropriate dressing 44, which may be a transparent film (Tegaderm) or similar dressing.

Figure 5:
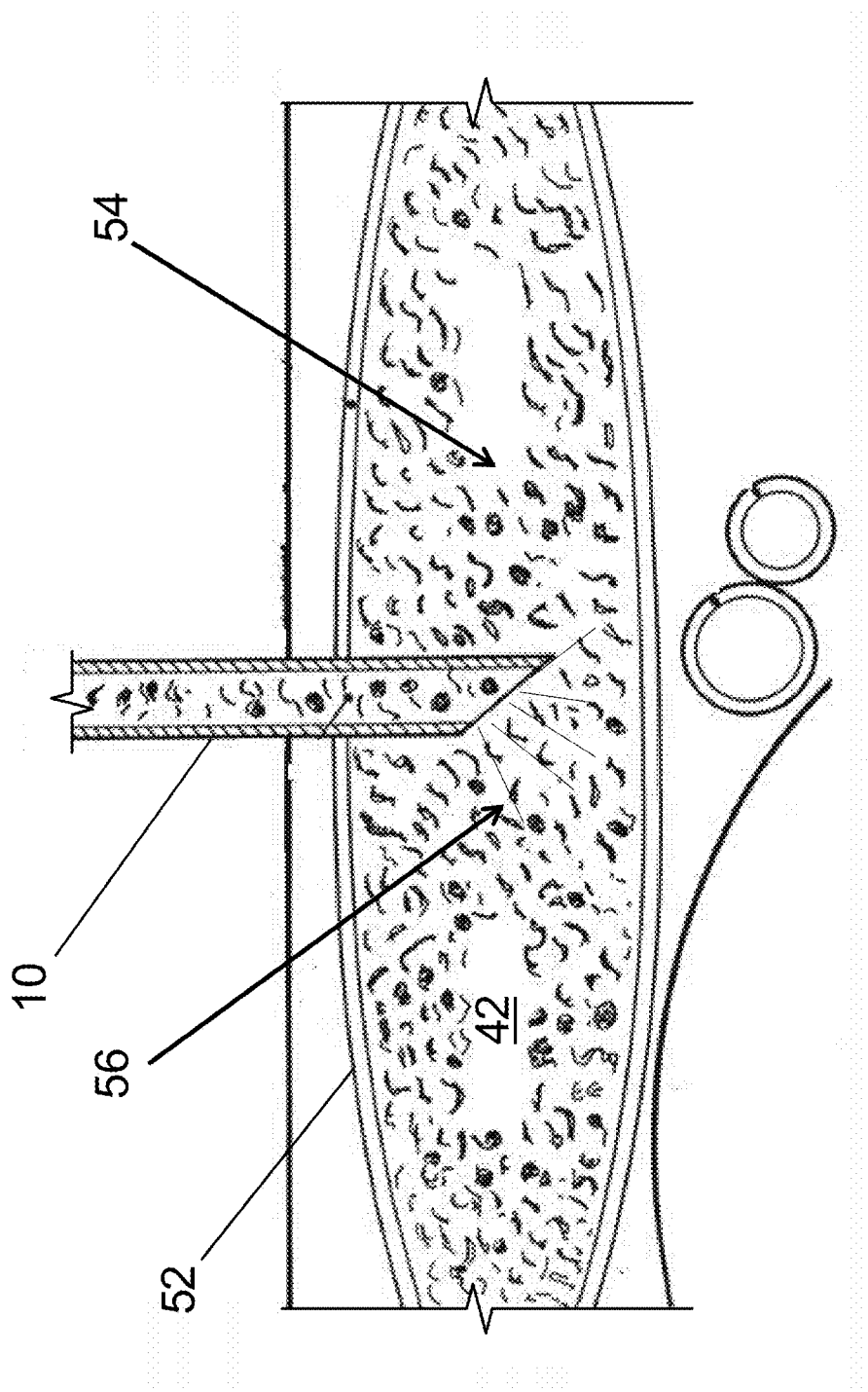
FIG. 5 shows a cross sectional view of the sternum showing the sternal intramarrow injection/infusion needle penetrating the sternum and injecting a therapeutic agent into the marrow.

As shown in FIG. 5, sternal intramarrow injection/infusion needle 10 is in place for bone marrow aspiration and sternal intramarrow injection/infusion of therapeutic agent 56 into sternal marrow cavity 54. Once IMIN needle assembly 30 is secured, aspiration of the marrow and introduction of chemotherapeutic agents, or other agents such as blood and blood products, can begin.

IMIN needle assembly 30 is designed to obtain bone marrow aspirate samples from the sternum as well as to inject chemotherapeutic or other agents into the sternal marrow. With regard to the rate at which the therapeutic agent 56 is introduced into the sternal marrow cavity 54, 1-2 minutes is generally necessary for complete sternal intramarrow injection of therapeutic agent 56. Dosages are provided in Example 1.

With regard to FIGS. 6A-6E, posterior iliac intramarrow injection/infusion needle 66 may have an overall length of 100 mm, and a uniform external diameter of 2.55 mm, except for the distal 2-3 mm portion where it is beveled to be in line with the stilette 76. In an alternative embodiment, at the junction of posterior iliac intramarrow injection/infusion needle 66 and stilette 76, multiple surface flutes 70 are provided (see FIG. 7B). Flutes 70 facilitate boring through the hard cortical bone 52 during its insertion of posterior iliac intramarrow injection/infusion needle 66 into the marrow cavity. The design of the fluted needle is described has been included in a publication by Islam (J Clin Pathol 0:1-3 (2016)).

As shown in FIG. 6A, the proximal end of posterior iliac intramarrow injection/infusion needle 66 has been fitted with a T-bar handle 62, which is ergonomically designed for an easy fitting and firm grip. The top of T-bar handle 62 may be round and slightly convex to receive the bottom concave part of the stilette handle 72. The central area of the T-bar handle 62 has an aperture to receive the nozzle of a syringe 110 (See FIG. 9) to complete the bone marrow injection/aspiration procedure.

As shown in FIG. 6D, stilette 76 may be a solid shaft of 2.1 mm in diameter except for the distal portion where it ends with a 3.0 mm long, three-faceted, sharply pointed stilette tip 78, which projects beyond the distal end of posterior iliac intramarrow injection/infusion needle 66 when inserted into the assembly. The proximal end of the stilette 76 is fitted with a solid plastic stilette handle 72. Its proximal (top) portion may be smooth and convex.

The proximal end of the stilette 76 may fitted with a male luer lock buried inside the dome handle to fit the female luer lock of posterior iliac intramarrow injection/infusion needle 66. A preferred embodiment of posterior iliac intramarrow injection/infusion needle 66, which includes at least one side aperture, has a distal 2-3 mm portion circumferentially beveled to be in line with the cutting tip 78 when it is in place within the lumen of multi aperture posterior iliac intramarrow injection/infusion needle 66.

Posterior iliac intramarrow injection/infusion needle may have multiple side apertures 122 at the distal end (see FIGS. 6A-6C). Posterior iliac intramarrow injection/infusion needle 66 may have an overall length of 60 mm (for using at the anterior iliac crest) and 120 mm (for using at the posterior iliac crest), a uniform external diameter of 3.0 mm, and a constant internal diameter of 1.5 mm except for the distal 1.25 mm where it is beveled to 18°. Each side aperture 122 may be made at 3 mm apart and drilled in a spiral fashion. The diameter of each side aperture 122 may be 1.3 mm. The one most distal aperture may be made 3.0 mm from distal end of posterior iliac intramarrow injection/infusion needle 66, which may be beveled.

The proximal end of posterior iliac intramarrow injection/infusion needle 66 has been fitted with a large T-bar handle specially shaped for firm grip and a standard female luer lock to receive the nozzle of a syringe/infusion set and to fit the male luer lock of the stilette 76 and handle. The stilette 76 may be a solid steel rod (1.3 mm in diameter and 63 & 123 mm in length) with a three faceted sharp pointed cutting tip 78 which projects beyond the tip of multi aperture posterior iliac intramarrow injection/infusion needle 66 and provides means of easy penetration of the soft tissue and bony cortex.

Figure 9:
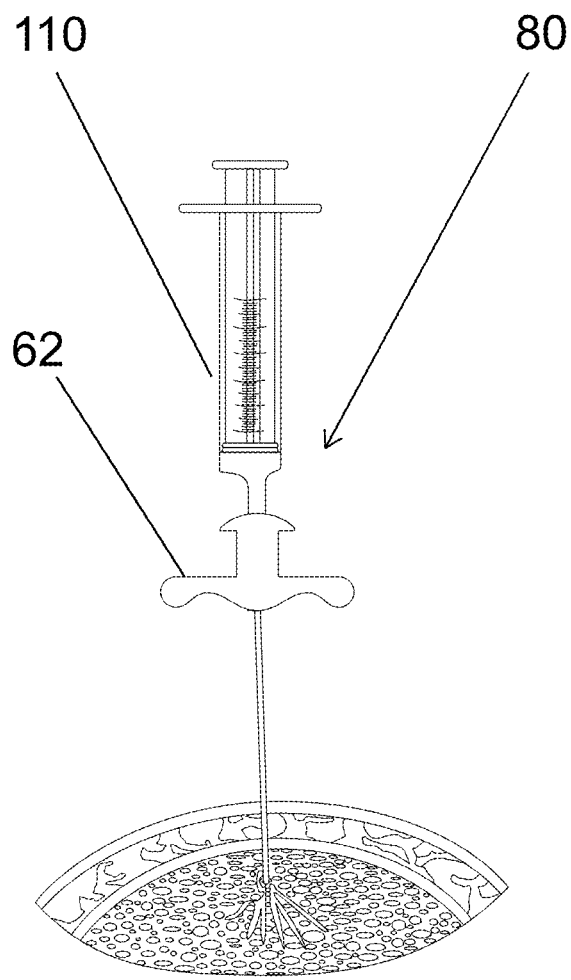
FIG. 9 shows a side view of the posterior iliac intramarrow injection/infusion needle assembly with a syringe containing the therapeutic agent attached to the assembly.

As shown in FIG. 9, posterior iliac intramarrow injection/infusion needle assembly 80 has been designed to obtain bone marrow aspirate samples from the ilium as well as to inject chemotherapeutic or other agents into the ilial marrow.

Figure 7B:
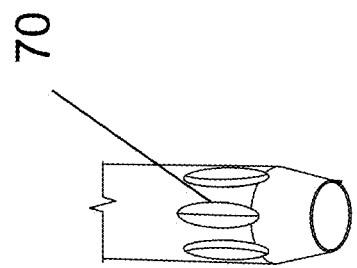
FIG. 7B shows a perspective view of an alternative embodiment of the distal end of the posterior iliac intramarrow injection/infusion needle with flutes.
Figure 7A:
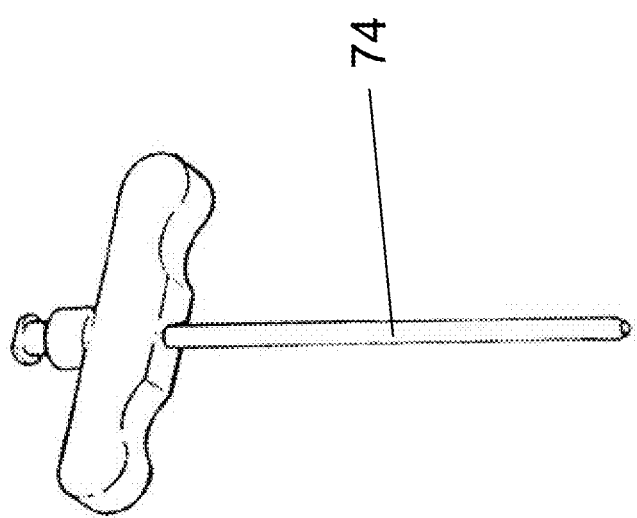
FIG. 7A shows a perspective view of an alternative embodiment of the posterior iliac intramarrow injection/infusion needle without side apertures.

With regard to FIGS. 7A and 7B, alternative features of the present disclosure are shown. These include a posterior iliac intramarrow injection/infusion needle without side apertures 74 (shown in FIG. 7A), and a posterior iliac intramarrow injection/infusion needle with flutes 70 (shown in FIG. 7B).

Figure 8:
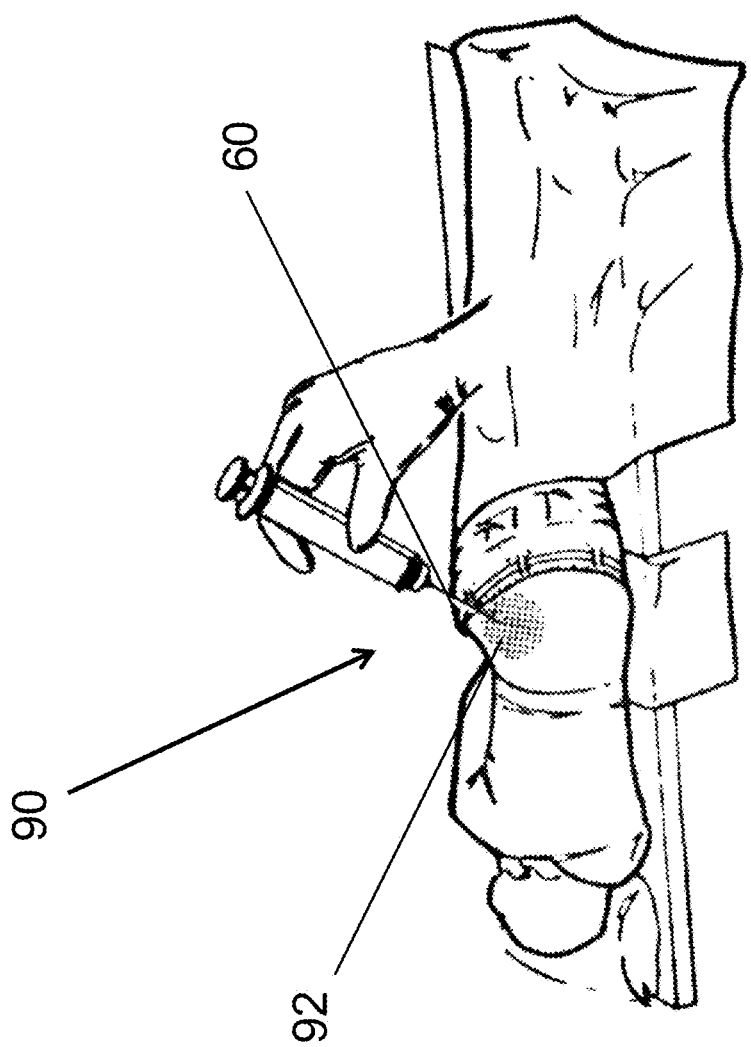
FIG. 8 shows a perspective view of the location of injection of anesthetic into the posterior iliac region where the posterior iliac intramarrow injection/infusion needle will be introduced.

With regard to FIG. 8, shown is injection of the anesthetic 90 with an anesthetic injection assembly 60 prior to injection of a therapeutic agent, in the posterior ilium. The injection takes place in a region below the posterior superior iliac spine 92. The first injection is given at the posterior ilium, and prior to the injection approximately 5-7 ml of bone marrow may be aspirated.

With regard to FIG. 9, posterior iliac intramarrow injection/infusion needle assembly 80 is shown. FIG. 9 shows the assembly with a posterior iliac intramarrow injection/infusion needle syringe 110. Following aspiration, the chemotherapeutic agent is injected into the posterior ilium marrow cavity 106 (shown in FIG. 10A) using the same posterior iliac intramarrow injection/infusion needle 66 as is used for aspiration, while posterior iliac intramarrow injection/infusion needle 66 is in place. With regard to injection into the general region of the posterior ilium 100, versus the sternum, posterior ilium marrow cavity 106 can accept a larger volume of chemotherapeutic agent, because it is the largest readily accessible area of marrow rich bone. Injection into posterior ilium marrow cavity 106 occurs prior to injection into the sternum in the preferred embodiment of the present disclosure.

For subsequent injections into the sternal marrow cavity 54 (see FIG. 5), rather than the posterior ilium marrow cavity 106 (shown in FIGS. 10A and 10B), chemotherapeutic agents can be directly injected without first aspirating the sternal marrow from the sternum 42. However, prior to injection into the sternal marrow it may be useful to draw a small amount of marrow to establish that sternal intramarrow injection/infusion needle 10 is within the marrow cavity and is not blocked.

With regard to the types of chemotherapeutic agents used in the present method, these include, but are not limited to Ara-C, Rituxan (Ritiximab) and Velcade (Bortezumib), for injection in the sternum and ilium. Other chemotherapeutic agents may be used within the scope of the present disclosure. The chemotherapeutic agents listed above have established records of safety, as all three have been used non-intravenously.

After puncture of the posterior ilium with posterior iliac intramarrow injection/infusion needle 66 is complete, therapeutic agents can be introduced into posterior ilium marrow cavity 106. With regard to injection/infusion in the posterior ilium, the flow rate necessary to achieve complete injection/infusion will generally require between 3 to 5 minutes (dosages are described in Example 1). With regard to sternal intramarrow injection/infusion, sternal intramarrow injection/infusion needle 10 needle may remain within the respective marrow cavity for a week or longer depending on the treatment protocol.

Introduction of chemotherapeutic agents directly into the marrow cavity kills leukemic blast cells and may also induce necrosis, perpetuated by the death and destruction of the leukemic blast cells locally. The combination of these two mechanisms for reducing the number of cancerous cells may have beneficial affect with regard to the response and overall treatment outcome for the patient. Induction of necrosis likely has a synergistic effect on the treatment of patients with malignant disorders involving the bone marrow.

The first injection, after a first quantity of marrow is aspirated from the ilium, into the ilium contains a larger volume (for example 50 mg/m2 in 5-10 ml of normal saline) of chemotherapeutic agent (Ara-C) and is given in the posterior ilium using posterior iliac intramarrow injection/infusion needle 66. Subsequent injections into the sternal marrow cavity, after a quantity of marrow is aspirated from the sternal marrow cavity, containing a smaller volume (for example 25 mg/m$^2$ in 1-2 ml of normal saline) of chemotherapeutic agent, such as Ara-C, are given by sternal intramarrow injection/infusion needle 10. As shown in Example 1, this method of treatment obtained overwhelmingly positive results.

Figure 10A:
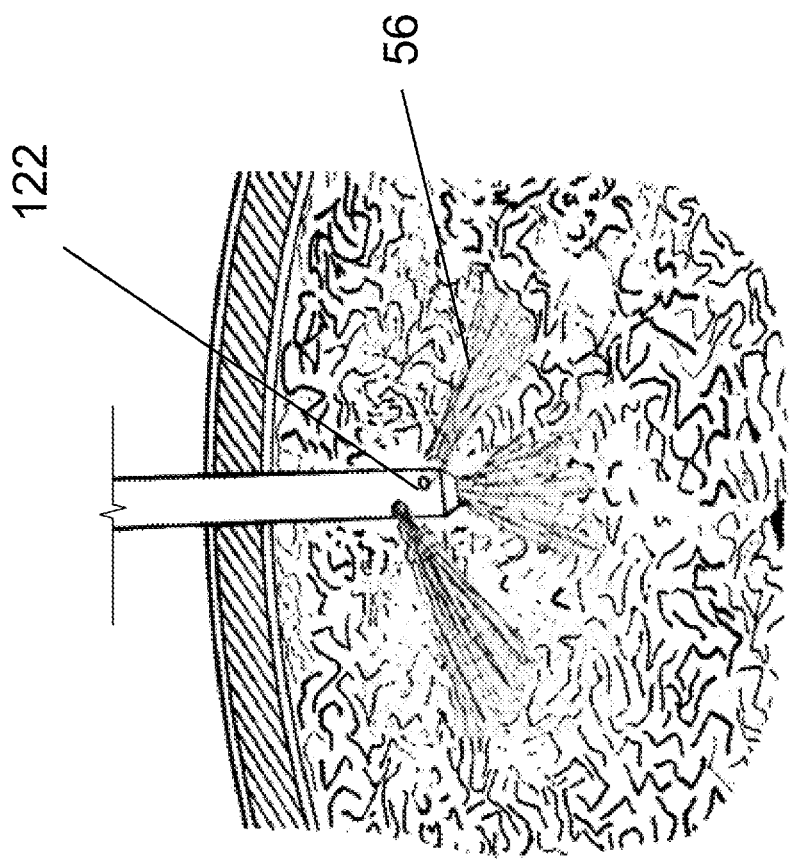
FIG. 10A shows a cross sectional view showing the posterior iliac intramarrow injection/infusion needle having punctured the posterior ilium.
Figure 10B:
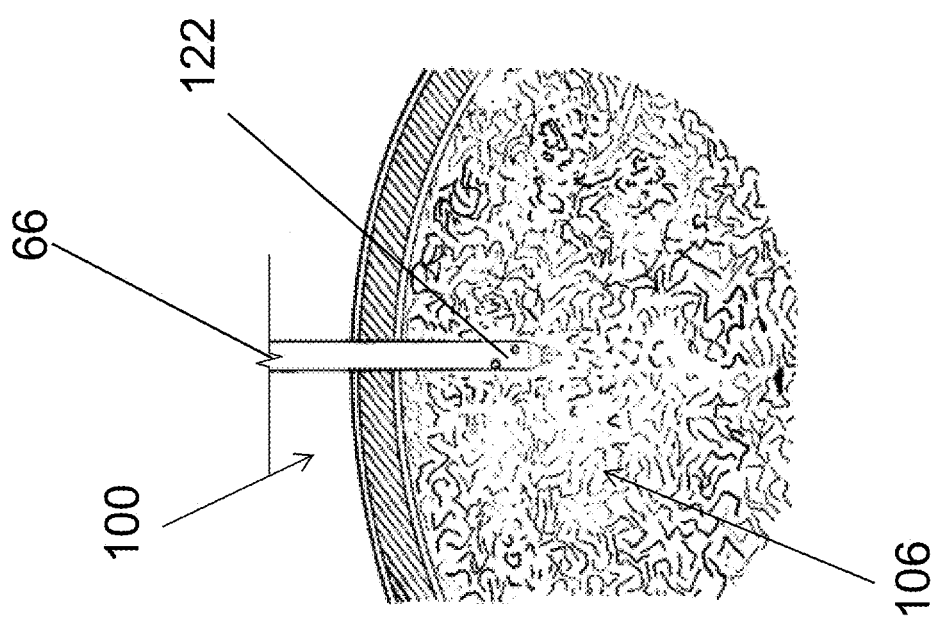
FIG. 10B shows a cross sectional view showing injection of chemotherapeutic agent into the marrow in the ilium from multiple apertures in the posterior iliac intramarrow injection/infusion needle.

With regard to FIGS. 10A and 10B, posterior iliac intramarrow injection/infusion needle 66 is shown in place in the posterior ilium marrow cavity 106 (ilium marrow cavity) after puncture of the posterior ilium 100. FIG. 10B shows a therapeutic agent 56 being injected into the posterior ilium marrow cavity 106 side apertures 122 of posterior iliac intramarrow injection/infusion needle 66.

Figure 11:
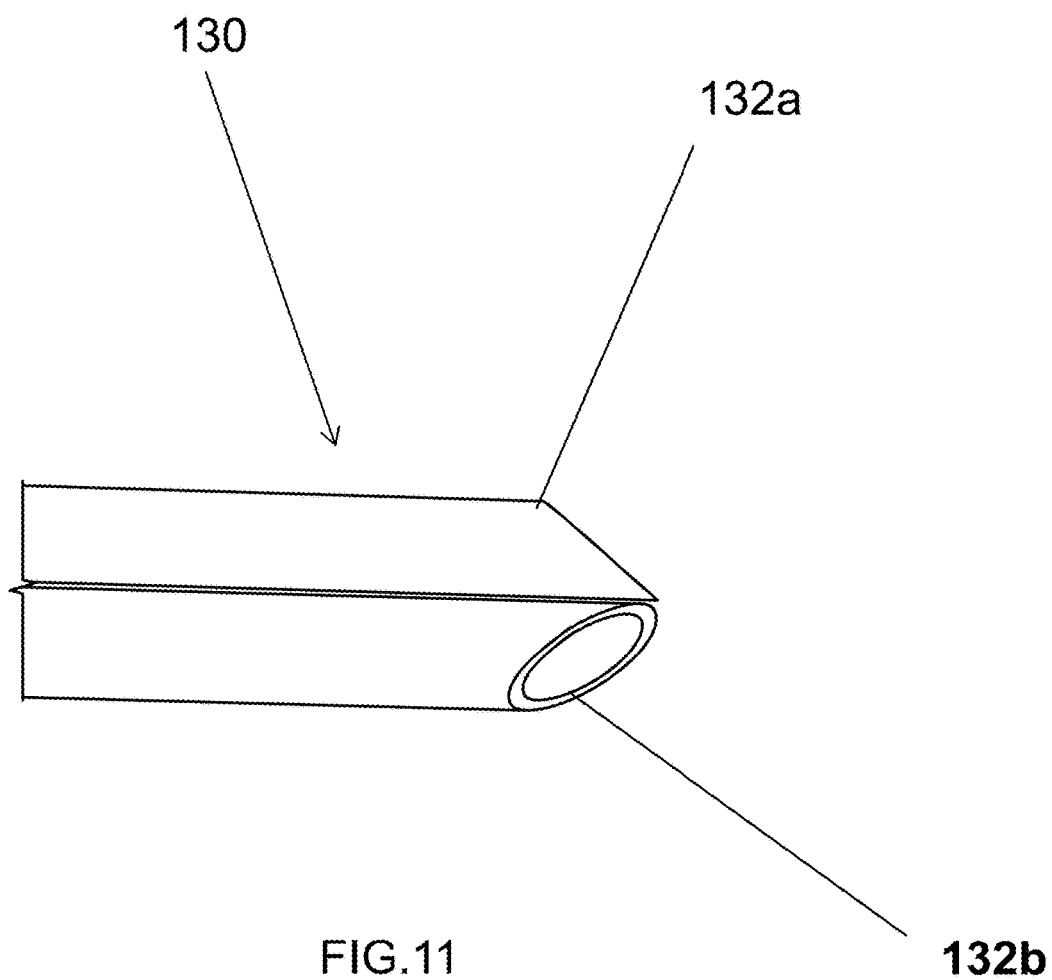
FIG. 11 shows a double barrel intramarrow injection/infusion needle.

With regard to FIG. 11, in one embodiment relating primarily to the sternum, a double barrel needle 130, having a first barrel and a second barrel, may be used to inject chemotherapeutic agents, blood and blood products if necessary through one barrel as well as withdraw materials such as bone marrow aspirate through the other barrel. Here, two identical needles 132a and 132b are fused together at the same point to create identical side by side needles attached to one another.

EXAMPLE 1

The patient, a 76-year-old white female, presented to the emergency room of hospital A with one month's history of generalized weakness, diarrhea, frequency of micturition, and decreased appetite. The patient also stated that she was sleeping almost 20 h a day and felt extremely lethargic. Her past medical history was significant for hypertension, diabetes mellitus, obesity, colitis, recto-vaginal fistula, gastroesophageal reflux disease (GERD), asthma, cellulitis, nephrolithiasis, Chronic Obstructive Pulmonary Disease (COPD), hiatal hernia, and atypical chest pain.

On physical examination, the patient was noted to be anemic, but she was not in acute distress. There was no jaundice, cyanosis, or edema. Her abdomen was soft and non-tender. Bowel sounds were heard. Liver, spleen, and kidneys could not be palpated due to abdominal obesity. There was no palpable lymphadenopathy. Heart sounds were normal. The chest was clear to auscultation and her vital signs were stable. The patient was afebrile.

Laboratory investigations revealed White Blood Cell (WBC) $42.5 \times 10^9$/L, hemoglobin 7.3 g/dL with normal Mean Corpuscular Volume (MCV), and Mean Corpuscular Hemoglobin (MCH) and a platelet count of $31 \times 10^9$/L. The differential counts revealed 15% segmented forms, 5% bands, 60% blasts and 13% lymphocytes, and 7% nucleated red blood cells. The peripheral blood smear revealed a frankly leukemic blood picture. Morphologically, the blast cells appeared to be myeloblasts.

Peripheral blood smear showed immature myeloid cells (myeloblasts). The bone marrow aspirate and flow cytometry confirmed the diagnosis of acute myeloblastic leukemia. The bone marrow aspirate revealed a highly cellular marrow (95%) with 64.5% myeloblasts, 0.5% promyelocytes, 10% myelocytes, 5% metamyelocytes, 2% bands, 4% neutrophils, 1% monocytes, and 4% lymphocytes, 0% basophils, 0% eosinophils, 0% plasma cells, and 9% erythroid precursors. Flow cytometry studies on the bone marrow aspirate sample revealed an abnormal blast cell population (58% of total events), which was "positive CD 117 (partial), CD 33, CD 13 (dim), and CD 56 while negative for CD 34, HLA-DR, CD 10, CD 19, CD 20, CD 22, CD 14, CD 64, CD 1a, CD 2, CD 3, and CD 7. There was some possible dim CD 15 expression".

Cytogenetic studies revealed an extremely low mitotic index. Only 14 metaphase spreads were available, which showed a normal female karyotype of 46, XX. No apparent clonal chromosomal aberrations were detected. Molecular studies revealed a NMP1 mutation in exon 12 of the gene. There was no evidence for either the FLT3 ITD or the codon 835/836 mutations.

After providing informed consent, the patient was treated with an intramarrow injection of Ara-C. The patient was premedicated with 100 mg of hydrocortisone and 50 mg of Benadryl intravenously half an hour before the intramarrow injection of Ara-C. The first injection of Ara-C (30 mg/m2) was given into the right posterior ilium. The subsequent intramarrow injections of Ara-C (25 mg/m2) were given into the sternum (each time a slightly different area of the sternum was chosen) once daily for 5 days. The patient tolerated the treatment procedure well and without any untoward effects, particularly nausea and vomiting which commonly occurs during Ara-C infusion.

On the day of first intramarrow injection, her WBC count was $71 \times 10^9$/L with 84% blast cells. Three days following the start of the treatment, her WBC count fell to $30 \times 10^9$/L and blast cell counts fell to 20%. Five days following the start of the treatment, her WBC count fell to $15 \times 10^9$/L and blast cell counts fell to 11%. At this stage, the peripheral blood smear also showed the appearance of few mature granulocytes.

The patient thus showed a dramatic response to intramarrow injection of Ara-C, particularly with respect to a rapid elimination of blast cells from the peripheral blood and perhaps also from the bone marrow. However, because of multiple comorbidities and socio-economic condition, the patient's family decided to discontinue her therapy and opted for hospice care. The patient expired a few days after she entered into hospice care. This circumstance precluded the opportunity to continue with our intramarrow injection therapy of Ara-C as per planned protocol (once daily for 5-7 days every 4-6 weeks) as well as to obtain the follow-up bone marrow assessments.

The new method of intramarrow injection/administration of Ara-C instead of the conventional intravenous or subcutaneous approach to induce remission in an elderly patient with AML has shown success. The approach of intramarrow injection/administration was chosen to provide a concentrated amount of chemotherapeutic agent (in this case Ara-C) directly into the marrow cavity of posterior ilium and sternum so that a large number of leukemic cells could be exposed to the chemotherapeutic agent. In addition, it was also postulated that a proportion of the injected chemotherapeutic agent into the hip bones or sternum, would also be absorbed via venous sinusoids and ultimately reach the malignant cells in distal bone marrow regions thus providing an enhanced and overall antineoplastic activity. The dose of Ara-C used (30 mg/m2 on day 1 at the right posterior ilium and the subsequent intramarrow injections of Ara-C (25 mg/m2) were given into the sternum once daily for 5 days) was considerably smaller than the standard 7+3 protocol (100 mg/m2/day for 7 days along with daunorubicin on days 1-3). The schedule used for the patient is, in fact comparable to the low-dose (20 mg/m2 subcutaneously for 10-14 days every 4-6 weeks) Ara-C protocol that is used for the treatment of elderly patients with AML (CA Cancer J Clin.; 52:363-371 (2002), J Clin Oncol. 28:562-569 (2010)) or relapsed or refractory AML patients (Am J Hematol. 83:185-188(2007)). The only difference between the low-dose Ara-C treatment and the intraosseous protocol is that the latter provides direct contact of the leukemic cells with Ara-C, thus affording a maximum killing effect of the leukemic cells. The small dose of Ara-C used may also have reduced the toxicity of the drug particularly nausea and vomiting.

Effectiveness of the method is evidenced by the fact that the leukemic blast cells were significantly reduced in number in the peripheral blood within days of starting the therapy. Clinically, the patient also felt better, and nausea and vomiting were absent.

EXAMPLE 2

The patient, an 85 years old white male, presented with two days history of chest pain and generalized weakness and mild short of breath. His past medical history was significant for cancer of the prostate, for colon cancer, status post colon resection, pulmonary embolism, DVT status post Greenfield filter placement, anemia and chronic kidney disease.

On physical examination the patient was noted to be anemic but he was not in acute distress. There was no jaundice, cyanosis or edema. His abdomen was soft and non-tender. Bowel sounds were heard. Liver, spleen and kidneys were not palpable. There was no palpable lymphadenopathy. Heart sounds S1 and S2 with soft ejection systolic murmur. The chest was clear to auscultation and his vital signs were stable. The patient was afebrile.

Laboratory investigations revealed WBC $15.6 \times 10^9$/L, hemoglobin 6.7 g/dL with normal MCV, and MCH and a platelet count of $82 \times 10^9$/L. Machine differential counts revealed 12% segmented forms, 12% lymphocytes, 73% monocytes. A manual differential of his peripheral blood smear revealed about 10% blasts and over 60% immature myelo-monocytic cells. A bone marrow aspirate revealed a frankly leukemic blood picture. Morphologically the blast cells appeared to be a combination of myeloblasts and monoblasts. The flow cytometry on the bone marrow confirmed the diagnosis of acute myeloid leukemia. The bone marrow aspirate revealed a highly cellular marrow (85%) with 20% myeloblasts, 35% monoblasts, 10% myelocytes, 10% promonocytes, 5% bands, 5% neutrophils, and 4% lymphocytes, 1% basophils, 0% eosinophils, 5% plasma cells and 5% erythroid precursors.

After providing informed consent the patient was treated with intramarrow injection of Ara-C. The patient was premedicated with 100 mg of hydrocortisone and 50 mg of Benadryl intravenously half an hour before the intramarrow injection of Ara-C. The first injection of Ara-C (30 mg/m2) was given into the right posterior ilium. The subsequent intramarrow injections of Ara-C (25 mg/m2) were given into the sternum (each time a slightly different area of the sternum was chosen) on three days a week. The patient tolerated the treatment procedure well and without any untoward affects, particularly nausea and vomiting which commonly occurs during conventional Ara-C infusion treatment.

On the day of first intramarrow injection his WBC count was $10 \times 10^9$/L with 70% leukemic cells. Five days following the start of the treatment his WBC count fell to $6.3 \times 10^9$/L and the leukemic cell counts fell to 40%. His platelet count was normalized ($160 \times 10^9$/L) and at this stage the peripheral blood smear also showed the appearance of few mature granulocytes.

The patient thus showed a dramatic response to intramarrow injection of Ara-C particularly with respect to a rapid elimination of blast cells from the peripheral blood and perhaps also from the bone marrow.

Although exemplary embodiments have been shown and described, it will be clear to those of ordinary skill in the art that a number of changes, modifications, or alterations to the disclosure as described may be made. All such changes, modifications, and alterations should therefore be seen as within the scope of the disclosure.

It is noted that terms like "specifically," preferably," "typically," "generally," and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

This application discloses several numerical ranges. The numerical ranges disclosed are intended to support any range or value within the disclosed numerical ranges even though a precise range limitation is not stated verbatim in the specification because this invention can be practiced throughout the disclosed numerical ranges. It is also to be understood that all numerical values and ranges set forth in this application are necessarily approximate.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

All documents cited in the Detailed Description of the invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

What is claimed is:

1. A needle assembly comprising:
    a sternal needle having a tip;
    the sternal needle wherein the tip is configured to safely penetrate a sternum;
    wherein the sternal needle has a shorter tip length than a conventional sternal needle;
    a winged grip attached to the sternal needle, wherein the winged grip has foldable wings that rotate between a vertical wing gripping configuration and a horizontal wing attachment configuration;
    wherein the winged grip is capable of supporting a force necessary to puncture the sternum with the sternal needle in the vertical wing gripping configuration;
    wherein the foldable wings are configured to accept an adhesive to hold a sternal needle assembly in place.

2. The needle assembly of claim 1, wherein the sternal needle is between 2 and 3 inches in length.

3. The needle assembly of claim 1, wherein the sternal needle is comprised of stainless steel of implantable grade.

4. The needle assembly of claim 1, wherein the sternal needle is connected to plastic tubing and a syringe.

5. A method of medical treatment comprising:
puncturing a posterior ilium with a posterior iliac needle;
injecting a therapeutic agent into an ilium marrow cavity;
puncturing a sternum with a sternal needle using force applied to the sternal needle through a handle with foldable wings, wherein the sternal needle is comprised of an implantable grade stainless steel and has a shortened tip relative to a conventional sternal needle, and wherein the sternal needle is attached to a sternal needle assembly having the handle with foldable wings, wherein the handle is formed by folding a first wing and a second wing vertically until the first wing makes contact with the second wing, and wherein the handle is capable of supporting a force necessary to puncture the sternum with the sternal needle;
unfolding the foldable wings into a position to where the foldable wings are parallel to and in contact with a patient's chest;
adhering the sternal needle assembly to the patient's chest with an adhesive tape covering at least a portion of the foldable wings and at least a portion of the patient's chest;
injecting the therapeutic agent into a sternal marrow cavity;
leaving the sternal needle assembly in place with the sternal needle in the sternal marrow cavity for at least 5 days during which at least one injection of the therapeutic agent is provided at intervals of at least one day.

6. The method of claim 5, wherein the therapeutic agent is Cytarabine, and an amount of Cytarabine injected into the posterior ilium is about 50 mg/m2 on a first day, and an amount of Cytarabine injected into the sternal marrow cavity is approximately 25 mg/m2 on subsequent days, wherein the amount of Cytarabine injected into the posterior ilium and the amount of Cytarabine injected into the sternal marrow cavity is sufficient to induce cell death.

7. The method of claim 5, wherein an amount of therapeutic agent injected into the posterior ilium and the sternal marrow cavity is sufficient to induce necrosis within an ilium marrow to assist in destruction of malignant cells and summon macrophages to induce further destruction of target cells.

8. A method of medical treatment comprising:
puncturing a posterior ilium with a posterior iliac needle having at least one aperture at a distal end of the posterior iliac needle;
injecting a chemotherapeutic agent into an ilium marrow cavity through the at least one aperture at a distal end of the posterior iliac needle;
forming a handle with foldable wings for a sternal needle assembly attached to a sternal needle by folding a first wing and a second wing vertically until the first wing makes contact with the second wing;
puncturing a sternum with the sternal needle using force applied to the sternal needle through the handle with foldable wings, wherein the sternal needle has a shortened tip relative to a conventional sternal needle, and wherein the handle with foldable wings is capable of supporting a force necessary to puncture the sternum with the sternal needle;
unfolding the foldable wings into a position to where the foldable wings are parallel to and in contact with a patient's chest;
adhering the sternal needle assembly to the patient's chest with an adhesive tape covering at least a portion of the foldable wings and at least a portion of the patient's chest;
injecting the chemotherapeutic agent into a sternal marrow cavity;
leaving the sternal needle assembly in place with the sternal needle in the sternal marrow cavity for at least 5 days during which at least one injection of the chemotherapeutic agent is provided at intervals of at least one day.

9. The method of claim 8, wherein aspiration of a marrow occurs prior to injection of chemotherapeutic agents into the ilium or sternal marrow cavity.

10. The method of claim 8, wherein a first quantity of marrow is aspirated from an ilium; after which wherein about 50 mg/m2 of therapeutic agent in 3-5 ml of normal saline is injected into the ilium marrow cavity using a posterior iliac needle on a first day; wherein a second quantity of marrow is aspirated from a sternum; after which wherein about 25 mg/m2 of therapeutic agent in 1-2 ml of normal saline is injected into a sternal marrow cavity using a sternal needle on days subsequent to the first day.

11. The method of claim 8, wherein the chemotherapeutic agent injected into the posterior ilium and the sternal marrow cavity induces necrosis within a marrow to assist in destruction of malignant cells and summon macrophages to induce further destruction of target cells.

12. The method of claim 8, wherein insertion of the sternal needle into a sternal marrow cavity involves first folding and gripping wing portions of a needle assembly by a thumb and index finger whereupon the sternal needle is slowly advanced towards a sternum so as to hit a cortical bone at a right angle between the sternal needle and the cortical bone while applying forward pressure to the sternal needle by hand, while concurrently rotating the sternal needle in a clockwise and counter-clockwise manner to improve penetration of sternal needle through the cortical bone and into the sternal marrow cavity as the sternal needle is advanced.

13. The method of claim 8, wherein the sternal needle is attached to a tube and a syringe.

14. The method of claim 8, wherein the sternal needle is introduced in a proximal region of the sternum at a level of a second intercostal space, in a mid-sternal line.

* * * * *